(12) United States Patent
Shintou et al.

(10) Patent No.: US 6,509,469 B1
(45) Date of Patent: Jan. 21, 2003

(54) PROCESS FOR THE PRODUCTION OF PYRIDINE DERIVATIVES

(75) Inventors: Taichi Shintou, Hiratsuka (JP); Fumiaki Ikeuchi, Hiratsuka (JP)

(73) Assignee: Sankio Chemical Co., Ltd., Tokyo (JP)

( * ) Notice: Subject to any disclaimer, the term of this patent is extended or adjusted under 35 U.S.C. 154(b) by 259 days.

(21) Appl. No.: 10/148,336

(22) PCT Filed: Nov. 14, 2000

(86) PCT No.: PCT/JP00/08025

§ 371 (c)(1),
(2), (4) Date: May 29, 2002

(87) PCT Pub. No.: WO01/40186

PCT Pub. Date: Jun. 7, 2001

(30) Foreign Application Priority Data

Nov. 30, 1999 (JP) ............................... 11-340729

(51) Int. Cl.[7] ...................... C07D 213/22; C07D 401/04
(52) U.S. Cl. ........................ 546/252; 546/167; 546/257
(58) Field of Search ................................. 546/252, 257, 546/167

(56) References Cited

FOREIGN PATENT DOCUMENTS

| | | |
|---|---|---|
| JP | 64-3169 | 1/1989 |
| WO | WO 98/52922 A1 | 11/1998 |

OTHER PUBLICATIONS

Gonsalves, et al. "Diels–Alder Reactions of 1,2,4–Triazines with Cyclic Vinyl Ethers" Tetrahedron vol. 49, No. 24, pp. 5277–5290, 1993.

Pfüller, et al. "The New and Simple 'LEGO' System for the Synthesis of Thienyl Substituted 2,6–Oligopyridines" Tetrahedron Letters, vol. 39, No. 48, pp. 8821–8824, 1998.

Pabst, et al. "The New and Simple 'LEGO' System: Its Application to the Synthesis of Superbranched Oligopyridines" Tetrahedron Letters, vol. 39, No. 48, pp. 8817–8820, 1998.

Sagi, et al. "Studies on as–triazine derivatives. XV. Intramolecular Reverse–Electron Demand Diels–Alder Reaction of 1,2,4–Triazine Derivatives." Heterocycles, vol. 30, No. 2, Special Issue, pp. 1009–1021, 1990.

Dittmar, et al. "(4+2)—Cycloaddition Der 1.2.4–Triazine—Ein Neuer Weg Zu 4–H–Azepinen." Tetrahedron Letters, No. 59, pp. 5171–5172, 1969.

Primary Examiner—Patricia L. Morris
(74) Attorney, Agent, or Firm—Sughrue Mion, PLLC

(57) ABSTRACT

Provided is a process for producing high-purity pyridine derivatives in a high yield at a low cost without causing pollution problems. Pyridine derivatives are produced by reacting 1,2,4-triazine compound with a vinyl carboxylate having a specific structure.

17 Claims, No Drawings

PROCESS FOR THE PRODUCTION OF PYRIDINE DERIVATIVES

TECHNICAL FIELD

The present invention relates to a process capable of producing, at a low cost in a high yield, high-purity pyridine derivatives serving as an important intermediate for the production of pharmaceuticals, agrichemicals, catalyst ligands, silver halide photosensitive materials, liquid crystals and electrophotography, and organic photosensitive materials or dyes used in the field of organic electroluminescence.

BACKGROUND ART

A variety of production processes of substituted pyridines have been reported. For example, reported is a process of condensing a pyridine compound and the N-oxide of another pyridine compound under heating in the presence of platinum-added Pd-C (Yakugaku Zasshi, 99(12), pp. 1176, 1181(1976)). The production yield is however low in this process. Also reported is cross-coupling reaction (Japanese Patent Laid-Open No. Sho 64-003169) making use of Grignard reaction, which is however accompanied with the such problems as difficulty in gaining or synthesizing a pyridine iodide compound necessary for obtaining a Grignard reagent of pyridines and necessity of special equipment.

In addition, proposed are Ullman condensation reaction of two pyridine halide compounds (Khim. Geol. Nauk., pp. 114(1970) and a process of cross-coupling a pyridine halide compound with a metal derivative in the presence of a Pd catalyst. For example, reported are cross-coupling with a borane derivative (Chem. Pharm. Bull., 33(11), pp. 4755 (1985), Heterocycles, 23(9), pp. 2375(1985)), cross-coupling with an alkyl tin derivative (Tetrahedron Lett., 33, pp. 2199(1992)) and cross-coupling with a pyridine halide compound in the presence of an Ni catalyst (WO9852922).

For mass production, however, they involve many problems such as high cost of the catalyst or reagent employed for the reaction and necessity of special treatment for the metal waste. Moreover, existence of many byproducts of these reactions makes separation difficult and a product pure enough to use as an intermediate for pharmaceuticals or electron materials have not yet been obtained.

A process for synthesizing pyridine derivatives from a 1,2,4-triazine compound by using 2,5-norbornadiene is conventionally known (for example, Tetrahedron Lett., 39, pp. 8817, 8821, 8825 (1988)).

Upon use for mass production, however, 2,5-norbornadiene is accompanied with many problems that a large excess, more specifically, at least 10 equivalents is required relative to the amount of a substrate, reaction is not completed in a short time, it is expensive, it is so toxic that even slight suction of it causes headaches, and it has a problem in stable supply on an industrial scale.

A process for obtaining pyridine compounds by using 1,2,4-triazine and vinyl acetate is reported (Tetrahedron Lett., 59, pp. 5171(1969)), but its yield is low and in addition, a substrate usable for this process is limited to highly active 1,2,4-triazine having an alkoxycarbonyl group at the 3,5,6-positions.

An object of the present invention is to provide a process for producing high-purity pyridine derivatives useful as an intermediate of pharmaceuticals, agrichemicals or liquid crystals in a high yield and at a low cost, in which the process does not generate pollution problems and can be carried out on an industrial scale.

DISCLOSURE OF THE INVENTION

According to the present invention, the below-described processes for producing pyridine derivatives are provided and the above-described objet of the present invention is attained.

(1) A process for producing a pyridine derivative, which comprises reacting a 1,2,4-triazine compound with a vinyl carboxylate represented by the following formula (I):

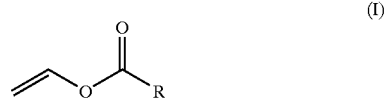

wherein R represents an alkyl group having at least 3 carbon atoms, a substituted or unsubstituted aryl group or a substituted or unsubstituted heterocyclic residue.

(2) The process for producing a pyridine derivative according to the item (1), wherein in the formula (I), R represents a alkyl group having 7 to 17 carbon atoms.

(3) The process for producing a pyridine derivative according to the item (1), wherein in the formula (I), R represents a substituted or unsubstituted phenyl group or a substituted or unsubstituted nitrogen-containing heterocyclic residue.

(4) The process for producing a pyridine derivative according to the item (1), which comprises reacting a 1,2,4-triazine compound represented by the following formula (III) with a vinyl carboxylate represented by the above-described formula (I):

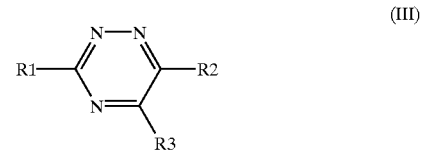

wherein R1, R2 and R3 may be the same or different and each represents a hydrogen atom, an alkyl group, an aryl group, a heterocyclic residue, an alkylthio group, an alkylsulfinyl group, an alkylsulfonyl group, an arylsulfinyl group, an arylsulfonyl group, an alkoxy group, a phenoxy group, an alkoxycarbonyl group or a phenoxycarbonyl group; R2 and R3 may be coupled together to form a ring.

(5) The process for producing a pyridine derivative according to the item (4), wherein in the formula (III), R1 represents a phenyl group or a nitrogen-containing heterocyclic residue.

(6) The process for producing a pyridine derivative according to the item (1), wherein the vinyl carboxylate is used in an amount of 1.01 to 20 moles per mole of the 1,2,4-triazine compound.

(7) The process for producing a pyridine derivative according to the item (1), wherein the vinyl carboxylate is used in. an amount of 1.5 to 5 moles per mole of the 1,2,4-triazine compound.

(8) The process for producing a pyridine derivative according to the item (1), wherein a reaction solvent having a boiling point of 100° C. or greater is employed.

(9) The process for producing a pyridine derivative according to the item (1), wherein a reaction solvent having a boiling point of 180 to 250° C. is employed.

(10) A process for producing a pyridine derivative, which comprises reacting a 1,2,4-triazine compound with a vinyl carboxylate derivative represented by the following formula (II):

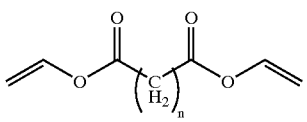

(II)

wherein n represents an integer of 0 to 18.

(11) The process for producing a pyridine derivative according to the item (10), wherein in the formula (II), n represents an integer of 3 to 12.

(12) The process for producing a pyridine derivative according to the item (10), which comprises reacting a 1,2,4-triazine compound represented by the following formula (III) with the vinyl carboxylate represented by the above-described formula (II):

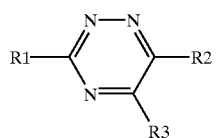

(III)

wherein R1, R2 and R3 may be the same or different and each represents a hydrogen atom, an alkyl group, an aryl group, a heterocyclic residue, an alkylthio group, an alkylsulfinyl group, an alkylsulfonyl group, an arylsulfinyl group, an arylsulfonyl group, an alkoxy group, a phenoxy group, an alkoxycarbonyl group or a phenoxycarbonyl group; R2 and R3 may be coupled together to form a ring.

(13) The process for producing a pyridine derivative according to the item (12), wherein in the formula (III), R1 is a phenyl group or a nitrogen-containing heterocyclic residue.

(14) The process for producing a pyridine derivative according to the item (10), wherein the vinyl carboxylate is used in an amount of 0.505 to 10 moles per mole of the 1,2,4-triazine compound.

(15) The process for producing a pyridine derivative according to the item (10), wherein the vinyl carboxylate is used in an amount of 0.75 to 2.5 moles per mole of the 1,2,4-triazine compound.

(16) The process for producing a pyridine derivative according to the item (10), wherein a reaction solvent having a boiling point of 100° C. or greater is employed.

(17) The process for producing a pyridine derivative according to the item (10), wherein a reaction solvent having a boiling point of 180 to 250° C. is employed.

BEST MODE FOR CARRYING OUT THE INVENTION

The present invention will hereinafter be described more specifically.

In the vinyl carboxylate represented by the formula (I) or (II), R represents a linear, branched or cyclic alkyl group having at least 3 carbon atoms, a substituted or unsubstituted aryl group or a substituted or unsubstituted heterocyclic residue. As the substituent for the aryl or heterocyclic residue, those having a Hammett σm substituent constituent falling within a range of −0.21 to 0.39 are usable. They may be monosubstituted or polysubstituted. When polysubstituted, substituents may be the same or different. Specific examples of the substituent having Hammett σm falling within a range of −0.21 to 0.39 include alkyl groups such as methyl and t-buytl, cycloalkyl groups such as cyclopentyl and cyclohexyl, aryl groups such as phenyl and naphthyl, alkoxy groups such as methoxy and ethoxy, amino groups such as amino and dimethylamino, a nitro group, and halogen atoms such as chlorine atom and bromine atom.

As R, examples of the linear, branched or cyclic alkyl groups having at least 3 carbon atoms, preferably at least 5 carbon atoms, more preferably 7 to 17 carbon atoms include propyl, isopropyl, butyl, isobutyl, s-butyl, t-buytl, butyl, pentyl, cyclopentyl, isopentyl, neopentyl, t-pentyl, 1-methylbutyl, 2-methylbutyl, 1-ethylpropyl, 1,2-dimethylpropyl, 2,2-dimethylpropyl, hexyl, cyclohexyl, 1-methylpentyl, 2-methylpentyl, 3-methylpentyl, 4-methylpentyl, 1-ethylbutyl, 2-ethylbutyl, 1,2-dimethylbutyl, 1,3-dimethylbutyl, 2,3-dimethylbutyl, 1,1-dimethylbutyl, 2,2-dimethylbutyl, 3,3-dimethylbutyl, 1-ethyl-2-methyl-propyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1,2-dimethylpentyl, 1,3-dimethylpentyl, 1,4-dimethylpentyl, 2,3-dimethylpentyl, 2,4-dimethylpentyl, 3,4-dimethylpentyl, 1,1-dimethylpentyl, 2,2-dimethylpentyl, 3,3-dimethylpentyl, 4,4-dimethylpentyl, 2-ethyl-1-methyl-butyl, 1-ethyl-2-methyl-butyl, 1-ethyl-3-methylbutyl, 1-ethyl-3-methylbutyl, 2-ethyl-3-methylbutyl, 1-ethyl-1-methylbutyl, 2-ethyl-2-methylbutyl, 1,2,3-trimethylbutyl, 1,1,2-trimethylbutyl, 1,2,2-trimethylbutyl, 1,1,3-trimethylbutyl, 1,3,3,-trimethylbutyl, 2,2,3-trimethylbutyl, 2,3,3-trimethylbutyl, 1-isopropyl-2-methylpropyl, octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-propylpentyl, 2-propylpentyl, 1-butylbutyl, 1,2-dimethylhexyl, 1,3-dimethylhexyl, 1,4-dimethylhexyl, 1,5-dimethylhexyl, 2,3-dimethylhexyl, 2,4-dimethylhexyl, 2,5-dimethylhexyl, 3,4-dimethylhexyl, 3,5-dimethylhexyl, 4,5-dimethylhexyl, 1,1-dimethylhexyl, 2,2-dimethylhexyl, 3,3-dimethylhexyl, 4,4-dimethylhexyl, 5,5-dimethylhexyl, 1,2,3-trimethylpentyl, 1,2,4-trimethylpentyl, 2,3,4-trimethylpentyl, 2-ethyl-1-methylpentyl, 3-ethyl-1-methylpentyl, 1-ethyl-2-methylpentyl, 3-ethyl-2-methylpentyl, 1-ethyl-3-methylpentyl, 2-ethyl-3-methylpentyl, 1-ethyl-4-methylpentyl, 2-ethyl-1-methylpentyl, 1-ethyl-1-methylpentyl, 2-ethyl-2-methylpentyl, 3-ethyl-3-methylpentyl, 1,2-diethylbutyl, 1,1-diethylbutyl, 2,2-diethylbutyl, nonyl, isononyl, s-nonyl, t-nonyl, neononyl, decyl, isodecyl, s-decyl, t-decyl, neodecyl, undecyl, isoundecyl, s-undecyl, t-undecyl, neoundecyl, dodecane, isododecane, s-dodecane, t-dodecane, neododecane, tridecyl, isotridecyl, s-tridecyl, t-tridecyl, neotridecyl, tetradecyl, isotetradecyl, s-tetradecyl, t-tetradecyl, neotetradecyl, pentadecyl, isopentadecyl, s-pentadecyl, t-pentadecyl, neopentadecyl, hexadecyl, isohexadecyl, s-hexadecyl, t-hexadecyl, neohexadecyl, heptadecyl, isoheptadecyl, s-heptadecyl, t-heptadecyl, neoheptadecyl, octadecyl, isooctadecyl, s-octadecyl, t-octadecyl, neooctadecyl, nonadecyl, isononadecyl, s-nonadecyl, t-nonadecyl and neononadecyl.

Examples of the aryl group as R include phenyl, naphthyl, tolyl, xylyl, cumenyl, mesityl, dimethylaminophenyl, diphenylaminophenyl, methoxyphenyl, phenoxyphenyl, cyclohexylphenyl, nitrophenyl, chlorophenyl, bromophenyl, fluorophenyl, iodophenyl, trifluorophenyl, hydroxyphenyl, carboxyphenyl, methyloxycarbonylphenyl and cyanophenyl.

Examples of the heterocyclic residue as R include pyridyl, pyrazinyl, pyrimidyl, quinolyl, isoquinolyl, pyrrolyl, pyrazolyl, imidazolyl, thienyl, furyl, thiazolyl, isothiazolyl, oxazolyl, isoxazolyl, methylpyridyl, phenylpyridyl, nitropyridyl, chloropyridyl, bromopyridyl, methoxypyridyl, diphenylaminopyridyl, methylpyrazinyl, phenylpyrazinyl, nitropyrazinyl, chloropyrazinyl, bromopyrazinyl, methoxypyrazinyl and diphenylaminopyrazinyl.

In the formula (II), n stands for an integer of 0 to 18, preferably 3 to 12.

When, in the formula (I), R represents an alkyl group having 1 or 2 carbon atoms, the reaction between the 1,2,4-triazine compound and vinyl carboxylate proceeds very slowly. Such an alkyl group is therefore unsuited for the industrial production of pyridine derivatives.

In the formula (I), R preferably represents a $C_{7-17}$ alkyl group. R representing a substituted or unsubstituted phenyl group or a substituted or unsubstituted nitrogen-containing heterocyclic residue is also preferred.

Specific preferred examples of R include propyl, isopropyl, butyl, isobutyl, s-butyl, t-butyl, pentyl, cyclopentyl, isopentyl, neopentyl, t-pentyl, 1-methylbutyl, 2-methylbutyl, 1-ethylpropyl, 1,2-dimethylpropyl, 2,2-dimethylpropyl, hexyl, cyclohexyl, 1-methylpentyl, 2-methylpentyl, 3-methylpentyl, 4-methylpentyl, 1-ethylbutyl, 2-ethylbutyl, 1,2-dimethylbutyl, 1,3-dimethylbutyl, 2,3-dimethylbutyl, 1,1-dimethylbutyl, 2,2-dimethylbutyl, 3,3-dimethylbutyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1,2-dimethylpentyl, 1,3-dimethylpentyl, 1,4-dimethylpentyl, 2,3-dimethylpentyl, 2,4-dimethylpentyl, 3,4-dimethylpentyl, 1,1-dimethylpentyl, 2,2-dimethylpentyl, 3,3-dimethylpentyl, 4,4-dimethylpentyl, octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylexyl, 4-ethylhexyl, 1-propylpentyl, 2-propylpentyl, 1-butylbutyl, 1,2-dimethylhexyl, 1,3-dimethylhexyl, 1,4-dimethylhexyl, 1,5-dimethylhexyl, 2,3-dimethylhexyl, 2,4-dimethylhexyl, 2,5-dimethylhexyl, 3,4-dimethylhexyl, 3,5-dimethylhexyl, 4,5-dimethylhexyl, 1,1-dimethylhexyl, 2,2-dimethylhexyl, 3,3-dimethylhexyl, 4,4-dimethylhexyl, 5,5-dimethylhexyl, 1,2-diethylbutyl, 1,1-diethylbutyl, 2,2-diethylbutyl, nonyl, isononyl, s-nonyl, t-nonyl, neononyl, decyl, isodecyl, s-decyl, t-decyl, neodecyl, phenyl, naphthyl, tolyl, xylyl, cumenyl, mesityl, nitrophenyl, chlorophenyl, bromophenyl, fluorophenyl, iodophenyl, trifluorophenyl, cyanophenyl, pyridyl, pyrazinyl, pyrimidyl, quinolyl, isoquinolyl, pyrrolyl, pyrazolyl, imidazolyl, thienyl and furyl.

As the 1,2,4-triazine compound, 1,2,4-triazine compounds represented by the following formula (III) are preferred.

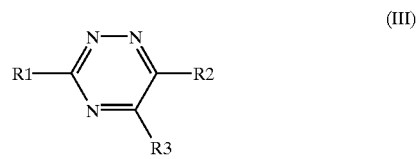

wherein, R1, R2 and R3 may be the same or different and each represents a hydrogen atom, an alkyl group, an aryl group, a heterocyclic residue, an alkylthio group, an alkylsulfinyl group, an alkylsulfonyl group, an arylsulfinyl group, an arylsulfonyl group, an alkoxy group, a phenoxy group, an alkoxycarbonyl group or a phenoxycarbonyl group; R2 and R3 may be coupled together to form a ring.

One embodiment of reacting the 1,2,4-triazine compound with the vinyl carboxylate will next be described specifically for detailed description of the invention process. It should however be noted that the scope of the present invention is not limited to or by it.

The reaction between the 1,2,4-triazine compound (III) and the vinyl carboxylate proceeds in accordance with the below-described reaction scheme, whereby the corresponding pyridine derivative (a) is produced.

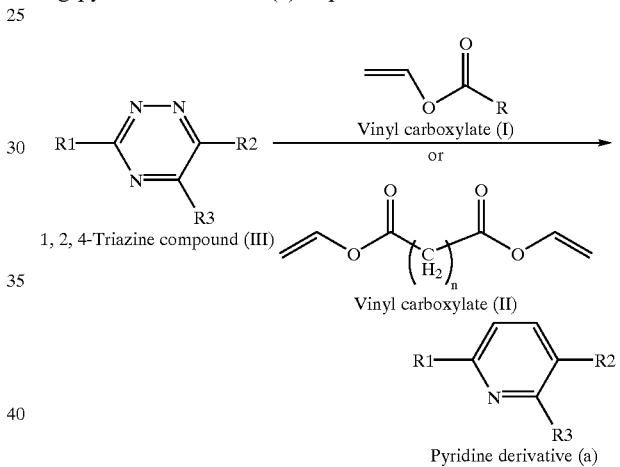

wherein, R has the same meaning as described above, n stands for an integer of 0 to 18, preferably an integer of 3 to 12, and R1, R2 and R3 have the same meanings as described above.

A detailed description will next be made of R1, R2 and R3 in the formulas (a) and (III).

As examples of the alkys group, linear or branched $C_{1-18}$ alkyl groups can be mentioned. Preferred examples include $C_{1-4}$ alkyl groups such as methyl, ethyl, propyl, isopropyl, butyl, isobutyl, sec-butyl and tert-butyl. Of these, a methyl group which can be introduced into a carboxylic acid or aldehyde is more preferred.

As the aryl group, substituted or unsubstituted phenyl groups, naphthyl group, anthryl group and phenanthryl group can be given. Preferred examples include substituted or unsubstituted phenyl groups and naphthyl groups, with substituted or unsubstituted phenyl groups being more preferred.

As examples of the substituent for the substituted aryl group, substituents having a Hammett σm substituent constituent falling within a range of −0.21 to 0.39 can be mentioned. They may be monosubstituted or polysubstituted. When polysubstituted, substituents may be the same or different. Specific examples of the substituent having Hammett σm falling within a range of −0.21 to 0.39 include alkyl groups such as methyl and t-butyl, cycloalkyl groups such as cyclopentyl and cyclohexyl, aryl groups such as phenyl and naphthyl, alkoxy groups such as methoxy and ethoxy, amino groups such as amino and dimethylamino, nitro group, and halogen atoms such as chlorine atom and bromine atom.

Specific examples of the heterocyclic residue include substituted or unsubstituted pyridyl, pyrazinyl, pyrimidyl, quinolyl, isoquinolyl, pyrrolyl, pyrazolyl, imidazolyl, thienyl, furyl, thiazolyl, isothiazolyl, oxazolyl and isoxazolyl groups. Of these, preferred are substituted or unsubstituted pyridyl, pyrazinyl, pyrimidyl, quinolyl, isoquinolyl, pyrrolyl and pyrazolyl groups, with substituted or unsubstituted pyridyl, pyrazinyl, pyrimidyl, quinolyl and isoquinolyl groups being more preferred.

As examples of the substituent for the substituted heterocyclic residue, substituents having a Hammett σm substituent constituent falling within a range of −0.21 to 0.39 can be mentioned. They may be monosubstituted or polysubstituted. When polysubstituted, substituents may be the same or different. Specific examples of the substituent having Hammett δm falling within a range of −0.21 to 0.39 include alkyl groups such as methyl and t-buytl, cycloalkyl groups such as cyclopentyl and cyclohexyl, aryl groups such as phenyl and naphthyl, alkoxy groups such as methoxy and ethoxy, amino groups such as amino and dimethylamino, nitro group, and halogen atoms such as chlorine atom and bromine atom.

Specific examples of the alkylthio group include linear or branched $C_{1-18}$ alkylthio groups, preferably $C_{1-4}$ alkylthio groups such as methylthio, ethylthio, propylthio, isopropylthio, butylthio, sec-butylthio and tert-butylthio, more preferably methylthio and ethylthio.

As examples of the alkylsulfinyl (—SOR) and alkylsulfonyl (—SO$_2$R) groups, alkylsulfinyl and alkylsulfonyl groups having similar alkyl groups to those of the alkylthio group can be given. Preferred are methylsulfinyl, ethylsulfinyl, methylsulfonyl and ethylsulfonyl groups.

As examples of the arylsulfinyl (—SOAr) group, arylsulfinyl groups having a substituted or unsubstituted aryl group can be given and preferred are benzenesulfinyl and toluenesulfinyl groups.

As examples of the substituent for the substituted arylsulfinyl group, substituents having a Hammett σm substituent constituent falling within a range of −0.21 to 0.39 can be mentioned. They may be monosubstituted or polysubstituted. When polysubstituted, substituents may be the same or different. Specific examples of the substituent having Hammett σm falling within a range of −0.21 to 0.39 include alkyl groups such as methyl and t-butyl, cycloalkyl groups such as cyclopentyl and cyclohexyl, aryl groups such as phenyl and naphthyl, alkoxy groups such as methoxy and ethoxy, amino groups such as amino and dimethylamino, nitro group, and halogen atoms such as chlorine atom and bromine atom.

As examples of the arylsulfonyl (—SO$_2$Ar) group, arylsulfonyl groups having a substituted or unsubstituted aryl group can be given and preferred are benzenesulfonyl and toluenesulfonyl groups.

As examples of the substituent for the substituted arylsulfonyl group, substituents having a Hammett σm substituent constituent falling within a range of −0.21 to 0.39 can be mentioned. They may be monosubstituted or polysubstituted. When polysubstituted, substituents may be the same or different. Specific examples of the substituent having Hammett σm falling within a range of −0.21 to 0.39 include alkyl groups such as methyl and t-buytl, cycloalkyl groups such as cyclopentyl and cyclohexyl, aryl groups such as phenyl and naphthyl, alkoxy groups such as methoxy and ethoxy, amino groups such as amino and dimethylamino, nitro group, and halogen atoms such as chlorine atom and bromine atom.

Specific examples of the alkoxy group include linear or branched $C_{1-18}$ alkoxy groups. Preferred are $C_{1-4}$ alkoxy groups such as methoxy, ethoxy, propoxy, isopropoxy, butoxy, isobutoxy, sec-butoxy and tert-butoxy, with linear $C_{1-4}$ alkoxy groups such as methoxy, ethoxy, propoxy and butoxy being more preferred.

As the alkoxycarbonyl (—COOR) group, the alkoxycarbonyl groups having the above-described alkoxy group can be mentioned. Preferred are methoxycarbonyl and ethoxycarbonyl groups.

In the formula (III), R1, R2 and R3 may be the same or different and preferred examples include a hydrogen atom, an alkyl group, an aryl group or a heterocyclic residue. As R1, alkyl, aryl and heterocyclic residue are more preferred, with phenyl and nitrogen-containing heterocyclic residue being especially preferred.

It is preferred that R2 and R3 represent the same group.

The 1,2,4-triazine compound which is a starting substance of the present invention can be prepared in any one of the following processes (1) to (4).

(1) A process for obtaining a 1,2,4-triazine compound by reacting a cyanoheterocyclic compound with a hydrazine and then reacting the amidrazone thus derived by the above reaction with a diketone (Tetrahedron Lett., 39, pp. 8817, 8821, 8825(1998)). A production process of a 1,2,4-triazine compound by adding water to this reaction system has already been found (Japanese Patent Application No. Hei 11-167308). One embodiment of it will be described next.

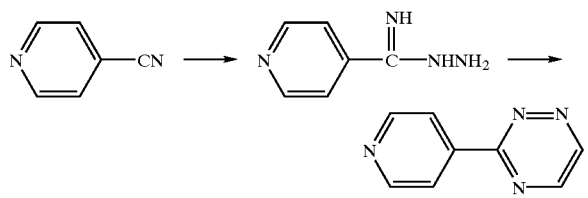

(2) A process for producing a 1,2,4-triazine compound through a cyanoheterocyclic compound, carbamate and then, amidorazone (J. Korean Chem. Soc., 39(9), pp. 755(1995)). One embodiment of it will be described next.

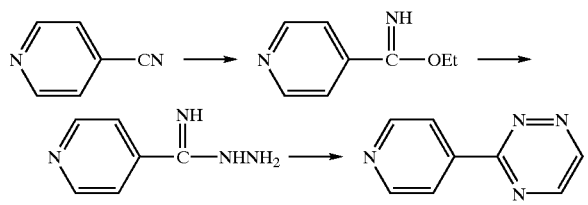

(3) A process for producing a 1,2,4-triazine compound by reacting an acid hydrazide and a diketone with ammonium acetate in an acetic acid solvent (Tetrahedron, 1, pp. 103(1957)). One embodiment of it will next be described.

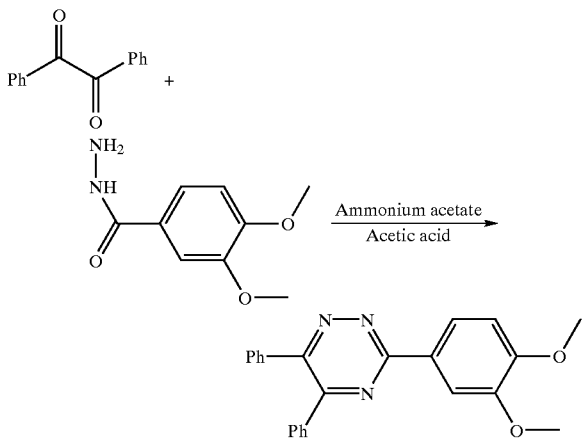

(4) A process for producing a 1,2,4-triazine compound by reacting an α-haloketone with an acid hydrazide (Tetrahedron, 33, pp. 1043(1977)). One embodiment of it will next be described.

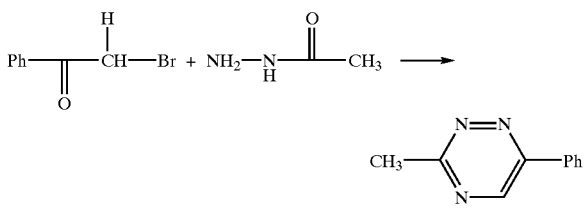

The vinyl carboxylate of the formula (I) or (II) usable in the present invention can be prepared readily from a carboxylic acid, which contains an alkyl group having at least 3 carbon atoms, a substituted or unsubstituted aryl group or a substituted or unsubstituted heterocyclic residue, by the process as described below, but the production process is not limited thereto. Such vinyl carboxylates are easily available because various ones are put on the market. Commercially available ones may be used as they are.

Examples of the production process of the above-described vinyl carboxylate include the direct vinylation process (J. Am. Chem. Soc., 69, pp. 2439(1947), J. Polymer. Sci., 1, pp. 207 (1951), Trans. Faraday Soc., 49, pp. 1108 (1953), U.S. Pat. No. 2,992,246 (1961), European Polymer J., 4, pp. 373(1968)), the vinyl exchange process (J. Org. Chem., 25, pp. 623(1960), Makromol. Chem., 73, pp. 173 (1964)), Makromol. Chem., 29, pp. 119(1959), J. Polymer Sci., 27, pp. 269(1958), Kobunshi Kagaku, 17, pp. 227 (1960), J. Sci. Eng. Res. Indian Inst. Technol. Kharagpur, 4, pp. 265(1990)), and the Halcon process (J. Am. Chem. Soc., 81, pp. 2552(1959)).

Specific examples of the vinyl carboxylate include vinyl butyrate, vinyl hexanoate, vinyl octanoate, vinyl decanoate, vinyl laurate, vinyl myristate, vinyl palmitate, vinyl stearate, vinyl cyclohexanecarboxylate, vinyl pivalate, vinyl octylate, vinyl monochloroacetate, divinyl adipate, vinyl methacrylate, vinyl crotonate, vinyl sorbate, vinyl benzoate, vinyl cinnamate, vinyl neodecanoate, vinyl neononanoate, vinyl 4-t-butylbenzoate, vinyl trifluoroacetate, vinyl-2-pyridine carboxylate, vinyl nicotinate, vinyl isonicotinate, vinyl-2-floate, vinyl 2-thiophenecarboxylate and divinyl adipate.

Of these, preferred are vinyl butyrate, vinyl hexanoate, vinyl octanoate, vinyl decanoate, vinyl laurate, vinyl myristate, vinyl palmitate, vinyl cyclohexanecarboxylate, vinyl pivalate, vinyl octylate, vinyl benzoate, vinyl neodecanoate, vinyl neononanoate, vinyl trifluoroacetate, and divinyl adipate, with vinyl hexanoate, vinyl octanoate, vinyl decanoate, vinyl laurate, vinyl cyclohexanecarboxylate, vinyl octylate, vinyl benzoate, vinyl neodecanoate, vinyl neononanoate, and divinyl adipate being especially preferred because of their easy separability after completion of the reaction.

There is no limitation imposed on the amount of the vinyl carboxylate insofar as it is at least an equimolar amount relative to the 1,2,4-triazine. The vinyl carboxylate of the formula (I) is usually used in an amount ranging from 1.01 to 20 moles, preferably 1.2 to 10.0 moles, more preferably 1.5 to 5.0 moles, each relative the 1,2,4-triazine (1 mole). The vinyl carboxylate of the formula (II), on the other hand, has two reaction sites in its molecule so that half the amount of the above case is sufficient for the progress of the reaction. Described specifically, the vinyl carboxylate of the formula (II) is usually employed in an amount ranging from 0.505 to 10 moles, preferably 0.6 to 5.0 moles, more preferably 0.75 to 2.5 moles, each relative to the 1,2,4-triazine (1 mole).

In the present invention, use of the reaction solvent is not indispensable, but preferred is a solvent having a boiling point of 100° C. or greater, more preferably 130 to 300° C., still more preferably 180 to 250° C.

As the reaction solvent, aromatic compounds are preferred.

The followings are aromatic compounds having a boiling point of 100° C. or greater and usable as the reaction solvent.
(i) Aromatic Hydrocarbon Compounds Toluene, xylene, diethylbenzene, diisopropylbenzene, ethylbenzene, propylbenzene, butylbenzene, 1-phenylhexane, chlorobenzene, dichlorobenzene, trichlorobenzene, bromobenzene, dibromobenzene, methoxybenzene, methoxyphenol, dimethoxybenzene, nitrobenzene, 1,4-cyclohexylbenzene, diphenylmethane, 1,2,3,4-tetrahydronaphthalene and the like.
(ii) Aromatic Heterocyclic Compounds 2,4-Dichloropyrimidine, 2,3,5-trichloropyridine, quinoline, quinazoline, 1,4-benzodioxane and the like.
(iii) Hydrogenated Aromatic Heterocyclic Compounds 1,2,3,4-Tetrahydroquinoline, 5,6,7,8-tetrahydroquinoline, 1,2,3,4-tetrahydroisoquinoline, 5,6,7,8-tetrahydroisoquinoline, 1-phenylpiperidine, 1-phenylpiperazine, indoline, julolidine and the like.

The followings are aliphatic compounds having a boiling point of 100° C. or greater and usable as a reaction solvent.
(iv) Saturated Aliphatic Compounds Octane, nonane, decane, undecane, dodecane, tridecane, ethylcyclohexane, 2-methyldodecane, 4-ethylundecane, tetradecane, pentadecane, 3,3-dimethyltridecane, hexadecane, heptadecane, 2-methyl-4-ethyltetradecane, and the like.
(v) Saturated Cyclic Aliphatic Compounds Dicyclohexyl, decahydronaphthalene, dodecahydrofluorene and the like.
(vi) Saturated Heterocyclic Aliphatic Compounds 1,3-Dimethyl-2-imidazolidinone (DMI), 1,4,7-trithiacyclononane, 1,4,7-trithiacyclodecane, 1,4,7,10-tetraoxacyclododecane, 1,4,7,10,13-pentaoxacyclopentadecane, 1,4,7-triazacyclononane and 1,4,7,10-tetraazacyclododecane.

These solvents may be used either singly or in combination as a reaction solvent.

Of the above-described reaction solvents, diethylbenzene, diisopropylbenzene, quinoline, nitrobenzene and 1,3- dimethyl-2-imidazolidinone (DMI) are preferred, with diisopropylbenzene and diethylbenzene being especially preferred. By the use of such a solvent, the reaction time can be shortened and the target compound can be obtained in a high yield.

The reaction solvent is usually employed in an amount ranging from 1 to 1000 ml, preferably 5 to 500 ml, more preferably 10 to 200 ml, relative to 0.1 mole of the 1,2,4-triazine.

The reaction temperature usually ranges from 80 to 350° C., preferably 120 to 300° C., more preferably 180 to 250° C. The disappearance of the 1,2,4-triazine compound can usually be confirmed when reaction is conducted for 3 to 6 hours.

After completion of the reaction, dilute hydrochloric acid is added to transfer the target compound to the water layer, followed by separation into layers. After the water layer is made basic, it is extracted into a solvent such as ethyl acetate or toluene. The solvent is then concentrated under reduced pressure. An alcohol or hexane is added to the residue to crystallize the same, whereby a high-purity pyridine derivative is available. Purification may be conducted through distillation.

Specific preferred examples of the pyridine derivatives available by the present invention will next be shown as (A-1) to (D-11). It should however be borne in mind that the present invention is not limited to or by them.

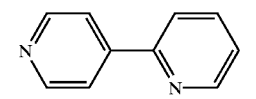 (A-1)

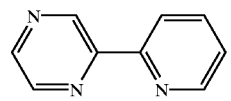 (A-2)

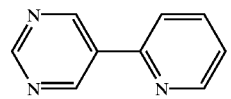 (A-3)

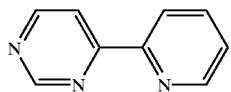 (A-4)

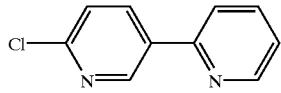 (A-5)

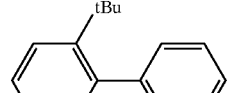 (A-6)

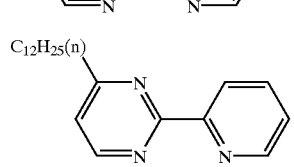 (A-7)

-continued

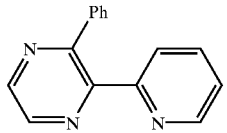 (A-8)

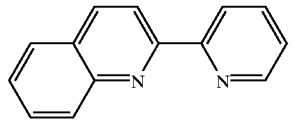 (A-9)

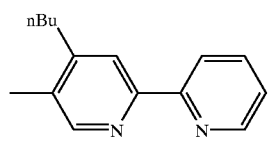 (A-10)

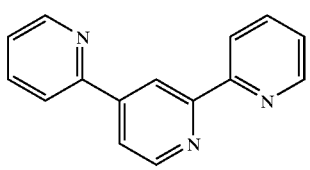 (A-11)

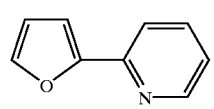 (A-12)

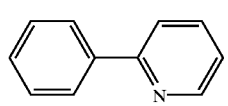 (A-13)

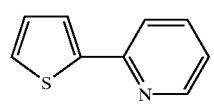 (A-14)

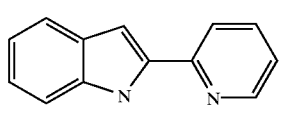 (A-15)

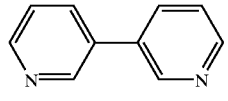 (A-16)

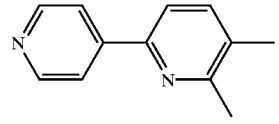 (B-1)

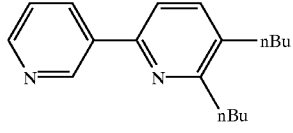 (B-2)

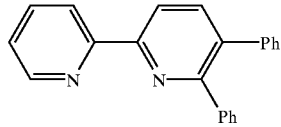 (B-3)

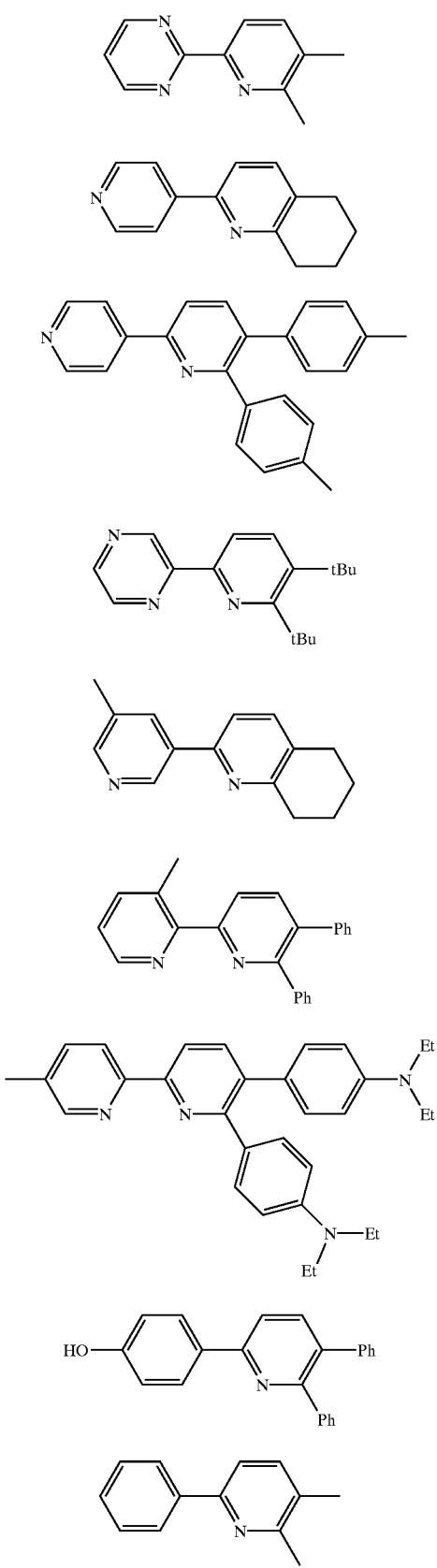
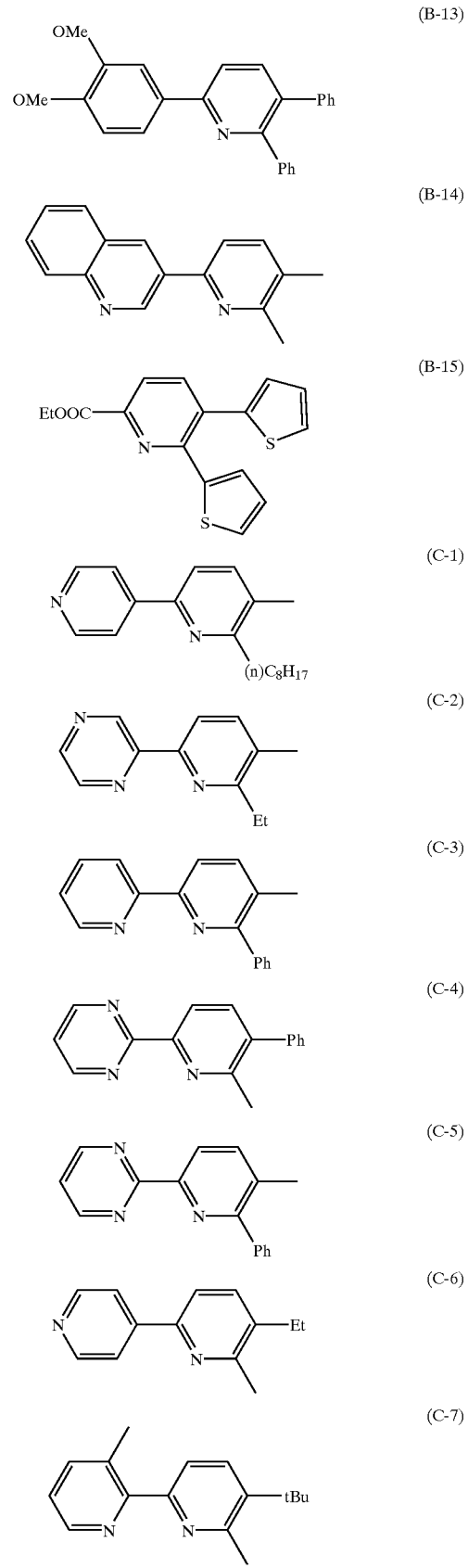

-continued

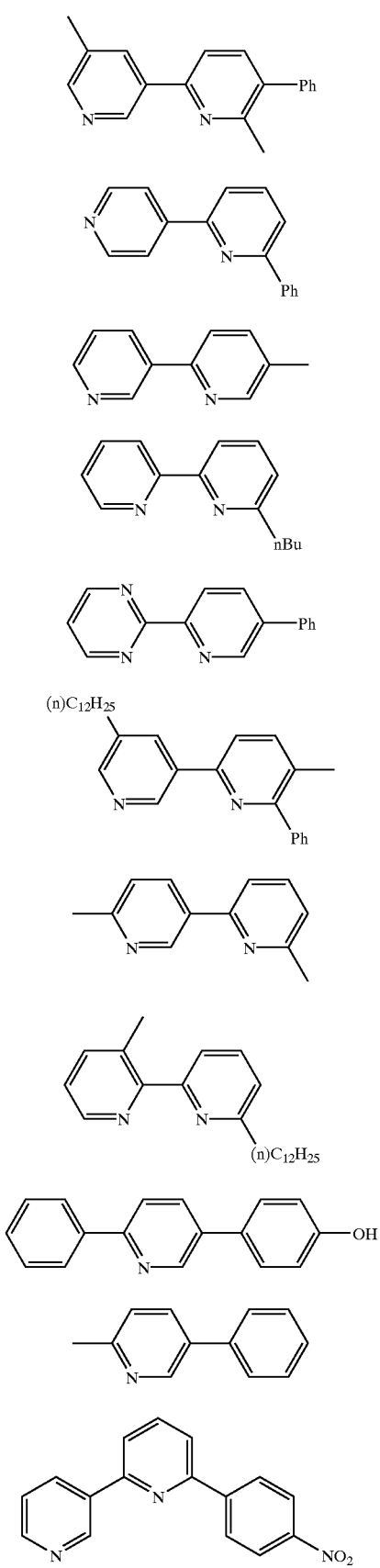

(C-8)
(D-1)
(D-2)
(D-3)
(D-4)
(D-5)
(D-6)
(D-7)
(D-8)
(D-9)
(D-10)

-continued

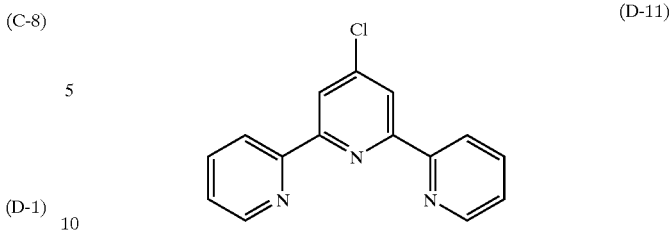

(D-11)

EXAMPLES

The present invention will hereinafter be described by Examples in further detail. It should however be borne in mind that the present invention is not limited to or by them. The purity was evaluated in accordance with high-performance liquid chromatography (which will hereinafter be abbreviated as "HPLC").

When the term "HPLC analysis" is used hereinafter, measurement is conducted under the below-described conditions. If any change, the changed conditions are described specifically.

(Measuring Conditions of HPLC Analysis)

Column: YMC-A-312

UV detector wavelength: 254 nm

Eluent: acetonitrile/water=25/75, containing acetic acid and triethylamine, each in an amount of 0.2 mass %, as a buffer.

Flow rate of the eluent: 1.0 ml/min

Synthesis Example 1

Synthesis of 3-(4-pyridyl)-1,2,4-triazine, a Starting Material

In a 2000-ml four-necked flask were charged 200 ml of water, 200.0 g (1.92 mole) of 4-cyanopyridine and 192.0 g (3.84 mole) of hydrazine monohydrate. The mixture was reacted for 4 hours under stirring at 50° C. After confirmation of the disappearance of the raw material by HPLC analysis, 400 ml of toluene was added and excessive hydrazine monohydrate was distilled off. This operation was conducted again. To the residue were successively added 800 ml of water and 278.4 g (1.92 mole) of a 40% aqueous glyoxal solution. The mixture was reacted for 2 hours at an external temperature of 100° C. After completion of the reaction, the reaction mixture was cooled to 5° C., whereby 222.4 g (yield: 85.2%) of the target compound was obtained as pale yellow crystals.

Example 1

Synthesis of 2,4'-dipyridyl (A-1)

In the next place, 45 ml of diisopropylbenzene, 25.0 g (0.158 mole) of the 3-(4-pyridyl)-1,2,4-triazine synthesized in Synthesis Example 1 and 60.1 g (0.316 mole) of vinyl n-decanoate were charged in a 500-ml four-necked flask. The resulting mixture was reacted under stirring at 210° C. for 2 hours. After confirmation of the disappearance of the raw material by HPLC, the reaction mixture was diluted with 100 ml of toluene and made acidic with 180 ml of 1 mole/l hydrochloric acid, followed by separation into layers. The resulting water layer was washed with 90 ml of toluene. This operation was conducted again. After the aqueous layer was made basic with 50 ml of 9 mole/l aqueous sodium hydroxide solution, it was extracted into 120 ml of toluene. The solvent was then distilled off under reduced pressure and the residue was crystallized from hexane, whereby 22.4 g (yield: 90.7%) of the target product was obtained as pale yellow crystals. As a result of HPLC analysis, the product was found to have a purity of 99.3%. Melting point: 60 to 62° C.

Examples 2 to 7

In a similar manner to Example 1 except for the use of the vinyl carboxylate as shown in Table 1 instead of vinyl n-decanoate, 2,4'-dipyridyl (A-1) was synthesized and its purity as measured by HPLC as well as its yield were evaluated.

Comparative Examples 1 and 2

In a similar manner to Example 1 except for the use of the vinyl carboxylate as shown in Table 1 instead of vinyl n-decanoate, synthesis was conducted.

Comparative Example 3

In a 500-ml four-necked flask were charged 145 ml of xylene, 25.0 g (0.158 mole) of 3-(4-pyridyl)-1,2,4-triazine and 146 g (1.58 mole) of 2,5-norbornadiene. The resulting mixture was reacted under reflux for 4 hours. After completion of the reaction, excessive 2,5-norbornadiene and xylene were distilled off under reduced pressure. The residue was crystallized from hexane, whereby 19.8 g (yield: 80.0%) of the target product was obtained as pale yellow crystals. As a result of HPLC analysis, its purity was found to be 99.2%.

Comparative Examples 4 and 5

In an autoclave were charged 45 ml of diisopropylbenzene, 25.0 g (0.158 mole) of 3-(4-pyridyl)-1,2,4-triazine and 60.1 g (0.316 mole) of vinyl acetate. The resulting mixture was reacted for each of 10 hours (Comparative Example 4) and 72 hours (Comparative Example 5) at 210° C. under stirring. At that time, the inner pressure increased to 1010 kPa. The above-described results are shown in Table 1.

TABLE 1

|  | To be reacted with | Reaction time (h) | Yield (%) | Purity (%) | Remarks |
| --- | --- | --- | --- | --- | --- |
| Example 1 | Vinyl n-decanoate | 2 | 90.7 | 99.3 |  |
| Example 2 | Vinyl n-octanoate | 3 | 90.7 | 99.2 |  |
| Example 3 | Vinyl n-hexanoate | 16 | 90.4 | 99.2 |  |
| Example 4 | Vinyl benzoate | 6 | 88.9 | 98.9 |  |
| Example 5 | Vinyl neononanoate | 3 | 91.4 | 99.0 |  |
| Example 6 | Vinyl pivalate | 48 | 87.8 | 98.8 |  |
| Example 7 | Vinyl n-butyrate | 42 | 88.6 | 98.5 |  |
| Example 8 | Vinyl 2-pyridine-carboxylate | 6 | 88.8 | 99.0 |  |
| Example 9 | Divinyl adipate | 2 | 91.5 | 99.0 |  |
| Example 10 | Vinyl palmitate | 2 | 90.1 | 99.1 |  |

TABLE 1-continued

|  | To be reacted with | Reaction time (h) | Yield (%) | Purity (%) | Remarks |
| --- | --- | --- | --- | --- | --- |
| Comp. Ex. 1 | Vinyl acetate | 72 | 9.2 | — | Reaction was not completed |
| Comp. Ex. 2 | Vinyl propionate | 72 | 15.2 | — | Reaction was not completed |
| Comp. Ex. 3 | 2,5-Norbornadiene | 4 | 80.0 | 99.2 |  |
| Comp. Ex. 4 | Vinyl acetate (reaction in Autoclave) | 10 | 10.0 | — | Reaction was not completed |
| Comp. Ex. 5 | Vinyl acetate (reaction in autoclave) | 72 | 10.4 | — | Reaction was not completed |

From the results as shown in Table 1, it has been revealed that:

By the process (Examples 1 to 10) according to the present invention, 2,4'-dipyridyl (A-1) can be synthesized in a high purity and a high yield.

The reaction is not completed in Comparative Examples 1 and 2 wherein the vinyl carboxylate of the formula (I) has carbon atoms as less as 1 or 2. Neither is the case in Comparative Example 4 and 5 wherein the reaction is conducted in an autoclave under pressure. Even if the post treatment is conducted while the reaction is not completed, separation using an acid or base does not proceed smoothly, resulting in a drop in a yield and purity.

In Comparative Example 3, the conventional process by reacting a 1,2,4-triazine compound with 2,5-norbornadiene was employed. The amount of 2,5-norbornadiene necessary for this reaction is at least 10 equivalents relative to 3-(4-pyridyl)-1,2,4-triazine. Necessity of a large amount of 2,5-norbornadiene and in addition, its expensiveness markedly raise the production cost compared with the invention process.

Examples 11 to 20

In a similar manner to Example 1 except for the use of the triazine derivatives as described below in Tables 2 and 3 instead of 3-(4-pyridyl)-1,2,4-triazine, pyridine derivatives were synthesized. After reaction for 3 hours in Examples 15, 16 and 19, and for 2 hours in the other Examples, the products were evaluated for their yields and, based on HPLC, their purities.

TABLE 2
| | Triazine derivative | Pyridine derivative | Yield (%) | HPLC Content (%) |
|---|---|---|---|---|
| Ex. 11 | 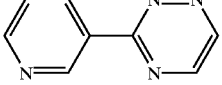 | 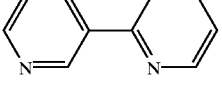 | 89.8 | 99.1 |
| Ex. 12 | 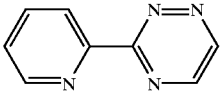 | 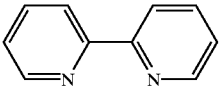 | 93.3 | 99.5 |
| Ex. 13 | 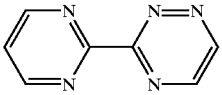 | 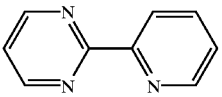 | 88.7 | 99.0 |
| Ex. 14 | 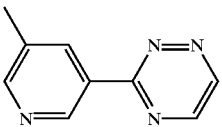 | 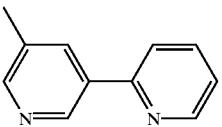 | 89.4 | 99.3 |
| Ex. 15 | 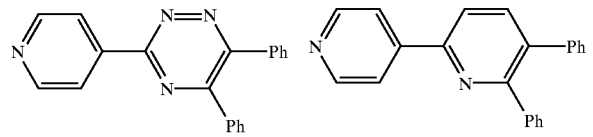 | 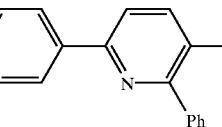 | 90.2 | 99.1 |
| Ex. 16 | 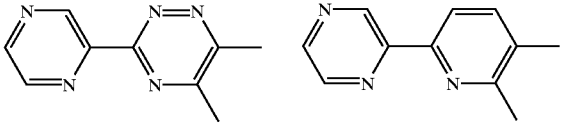 | 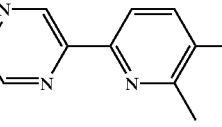 | 90.8 | 98.9 |
TABLE 3
| | Triazine derivative | Pyridine derivative | Yield (%) | HPLC content (%) |
|---|---|---|---|---|
| Ex. 17 | 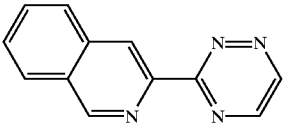 | 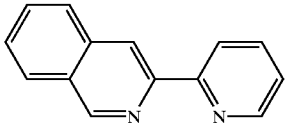 | 89.5 | 99.2 |
| Ex. 18 | 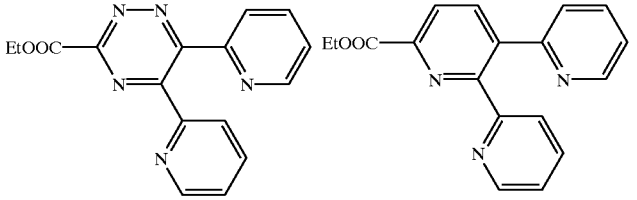 | 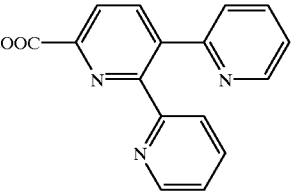 | 92.9 | 99.3 |
| Ex. 19 | 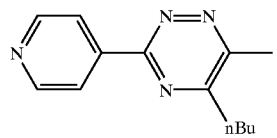 | 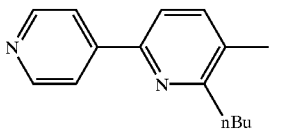 | 85.7 | 98.8 |

TABLE 3-continued

| | Triazine derivative | Pyridine derivative | Yield (%) | HPLC content (%) |
|---|---|---|---|---|
| Ex. 20 | 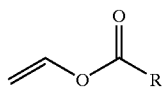 | 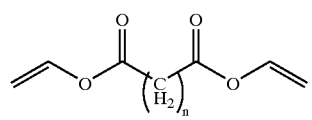 | 90.0 | 99.0 |

As is apparent from Tables 2 and 3, pyridine derivatives can be synthesized in a high yield and high purity according to the invention process.

<Industrial Applicability>

According to the process of the present invention, high-purity pyridine derivatives useful as an intermediate for pharmaceuticals, agrichemicals, catalyst ligands, silver halide photosensitive materials, liquid crystals and electrophotography, and for organic photosensitive materials and dyes in the field of organic electroluminescence can be produced in a high yield at a low cost. This process is free from pollution problems because no organic metal is used. Accordingly, the process of the present invention for producing pyridine derivatives has markedly high utility from the industrial viewpoint.

What is claimed is:

1. A process for producing a pyridine derivative, which comprises reacting a 1,2,4-triazine compound with a vinyl carboxylate represented by the following formula (I):

$$\text{(I)}$$

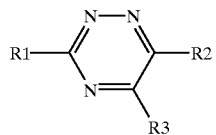

wherein R represents an alkyl group having at least 3 carbon atoms, a substituted or unsubstituted aryl group or a substituted or unsubstituted heterocyclic residue.

2. The process for producing a pyridine derivative according to claim 1, wherein in the formula (I), R represents a alkyl group having 7 to 17 carbon atoms.

3. The process for producing a pyridine derivative according to claim 1, wherein in the formula (I), R represents a substituted or unsubstituted phenyl group or a substituted or unsubstituted nitrogen-containing heterocyclic residue.

4. The process for producing a pyridine derivative according to claim 1, which comprises reacting a 1,2,4-triazine compound represented by the following formula (III) with a vinyl carboxylate represented by the above-described formula (I):

$$\text{(III)}$$

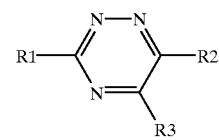

wherein R1, R2 and R3 may be the same or different and each represents a hydrogen atom, an alkyl group, an aryl group, a heterocyclic residue, an alkylthio group, an alkylsulfinyl group, an alkylsulfonyl group, an arylsulfinyl group, an arylsulfonyl group, an alkoxy group, a phenoxy group, an alkoxycarbonyl group or a phenoxycarbonyl group; R2 and R3 may be coupled together to form a ring.

5. The process for producing a pyridine derivative according to claim 4, wherein in the formula (III), R1 represents a phenyl group or a nitrogen-containing heterocyclic residue.

6. The process for producing a pyridine derivative according to claim 1, wherein the vinyl carboxylate is used in an amount of 1.01 to 20 moles per mole of the 1,2,4-triazine compound.

7. The process for producing a pyridine derivative according to claim 1, wherein the vinyl carboxylate is used in an amount of 1.5 to 5 moles per mole of the 1,2,4-triazine compound.

8. The process for producing a pyridine derivative according to claim 1, wherein a reaction solvent having a boiling point of 100° C. or greater is employed.

9. The process for producing a pyridine derivative according to claim 1, wherein a reaction solvent having a boiling point of 180 to 250° C. is employed.

10. A process for producing a pyridine derivative, which comprises reacting a 1,2,4-triazine compound with a vinyl carboxylate derivative represented by the following formula (II):

$$\text{(II)}$$

wherein n represents an integer of 0 to 18.

11. The process for producing a pyridine derivative according to claim 10, wherein in the formula (II), n represents an integer of 3 to 12.

12. The process for producing a pyridine derivative according to claim 10, which comprises reacting a 1,2,4-triazine compound represented by the following formula (III) with the vinyl carboxylate represented by the above-described formula (II):

$$\text{(III)}$$

wherein R1, R2 and R3 may be the same or different and each represents a hydrogen atom, an alkyl group, an aryl group, a heterocyclic residue, an alkylthio group, an alkylsulfinyl group, an alkylsulfonyl group, an arylsulfinyl group, an arylsulfonyl group, an alkoxy group, a phenoxy group, an alkoxycarbonyl group or a phenoxycarbonyl group; R2 and R3 may be coupled together to form a ring.

13. The process for producing a pyridine derivative according to claim 12, wherein in the formula (III), R1 is a phenyl group or a nitrogen-containing heterocyclic residue.

14. The process for producing a pyridine derivative according to claim 10, wherein the vinyl carboxylate is used in an amount of 0.505 to 10 moles per mole of the 1,2,4-triazine compound.

15. The process for producing a pyridine derivative according to claim 10, wherein the vinyl carboxylate is used in an amount of 0.75 to 2.5 moles per mole of the 1,2,4-triazine compound.

16. The process for producing a pyridine derivative according to claim 10, wherein a reaction solvent having a boiling point of 100° C. or greater is employed.

17. The process for producing a pyridine derivative according to claim 10, wherein a reaction solvent having a boiling point of 180 to 250° C. is employed.

* * * * *